United States Patent
Soman (10) Patent No.: US 11,291,647 B2
(45) Date of Patent: Apr. 5, 2022

(54) **PROCESS FOR PREPARATION OF $CO_2$ EXTRACT OF *AZADIRACHTA INDICA* AND HERBAL COMPOSITIONS THEREOF FOR TREATMENT OF CANCERS**

(71) Applicant: NISARGA BIOTECH PRIVATE LIMITED, Satara (IN)

(72) Inventor: Girish Sudhakar Soman, Satara (IN)

(73) Assignee: NISARGA BIOTECH PRIVATE LIMITED, Satara (IN)

( * ) Notice: Subject to any disclaimer, the term of this patent is extended or adjusted under 35 U.S.C. 154(b) by 91 days.

(21) Appl. No.: 16/557,294

(22) Filed: Aug. 30, 2019

(65) Prior Publication Data

US 2020/0069636 A1 Mar. 5, 2020

Related U.S. Application Data

(60) Provisional application No. 62/724,718, filed on Aug. 30, 2018.

(51) Int. Cl.

| | |
|---|---|
| *A61K 36/00* | (2006.01) |
| *A61K 31/343* | (2006.01) |
| *A61K 36/58* | (2006.01) |
| *A61K 31/08* | (2006.01) |
| *A61K 31/58* | (2006.01) |
| *A61K 31/335* | (2006.01) |
| *A61K 9/00* | (2006.01) |

(52) U.S. Cl.
CPC .......... *A61K 31/343* (2013.01); *A61K 9/0053* (2013.01); *A61K 31/08* (2013.01); *A61K 31/335* (2013.01); *A61K 31/58* (2013.01); *A61K 36/58* (2013.01); *A61K 2236/333* (2013.01); *A61K 2236/37* (2013.01); *A61K 2236/39* (2013.01); *A61K 2236/51* (2013.01)

(58) Field of Classification Search
CPC ...................... A61K 2236/37; A61K 2236/333
See application file for complete search history.

(56) References Cited

U.S. PATENT DOCUMENTS 5,370,873 A    12/1994  Udeinya

FOREIGN PATENT DOCUMENTS

| CN | 101972246 A | | 2/2011 |
|---|---|---|---|
| CN | 103864876 A | | 6/2014 |
| CN | 106344456 A | * | 1/2017 |
| JP | 2009274956 A | | 11/2009 |
| WO | WO20070137389 A1 | | 12/2007 |
| WO | WO2015035199 A1 | | 3/2015 |

* cited by examiner

*Primary Examiner* — Qiuwen Mi (74) *Attorney, Agent, or Firm* — Kramer & Amado, P.C.

(57) ABSTRACT

The present invention discloses process for preparation of a $CO_2$ extract of *Azadirachta indica* and herbal compositions thereof for the treatment of Oral and Colon cancers. More particularly, the invention discloses a process for preparation of a standardized $SCO_2$ extract of *Azadirachta indica* leaves and herbal compositions of the same for oral use.

9 Claims, 7 Drawing Sheets
(5 of 7 Drawing Sheet(s) Filed in Color)

PROCESS FOR PREPARATION OF $CO_2$ EXTRACT OF *AZADIRACHTA INDICA* AND HERBAL COMPOSITIONS THEREOF FOR TREATMENT OF CANCERS

TECHNICAL FIELD

The present invention relates to process for preparation of $CO_2$ extract of *Azadirachta indica* and herbal compositions thereof for the treatment of Oral and Colon cancers. More particularly, the invention relates to a process for preparation of standardized $SCO_2$ extract of *Azadirachta indica* leaves and herbal compositions of the same for oral use.

BACKGROUND AND PRIOR ART

Oral cancers are among the top three types of cancers in India. It appears as a growth or sore in the mouth that does not cure and includes cancers of the lips, tongue, cheeks, floor of the mouth, hard and soft palate, tongue, sinuses, and pharynx. The most common type of oral cancer is Squamous cell carcinoma.

According to the statistics, in 2012 the incidence of oral cancer in India was 53842 in males and 23161 in females. In India, the prevalence is high (20/100,000 population) and incidence is expected to rise by 2030. The international agency for research on cancer has predicted that India's incidence of cancer is from 1 million in 2012 and likely to be more than 1.7 million in 2035. This indicates that the death rate because of cancer will also increase from 1 million to 1-2 million in the same period. Incidence of oral cancer is more in men. Its incidence also increases by age with most of the oral cancer occurring in 50 to 70 years of age.

Globally, lip, oral cavity, and pharyngeal cancers had accounted for about 3.8% of all cancer cases and 3.6% of overall cancer deaths as per 2012 data. According to GLOBOCAN 2012, lip and oral cavity cancer is the $12^{th}$ most common cancer in Asia and ranks $8^{th}$ among all the cancers in men. In Asia and America, the incidence rates are 3.8% and 1.7% respectively, while mortality rate are 2.2% and 1% respectively.

Various etiological factors like tobacco consumption either smokeless tobacco or smoking and alcohol consumption had attributed to the high incidence of oral cancer in India. Also, positive family history of oral cancer, viral infections like HPV, poor oral hygiene, dietary deficiencies, and oro-dental factors are the other contributing factors.

Oral cancer can be detected by symptoms like pain in throat, long-standing ulcers in the mouth, loosening of teeth, and change in voice and difficulty in chewing and swallowing.

Colorectal cancer (CRC), also known as colon cancer or bowel cancer, is one of the leading causes of mortality and morbidity from cancer. Worldwide, it is the third most common cancer in men (10.0% of all cancer cases) and the second most common in women (9.4% of all cancer cases) with 60% of all cases encountered in developed countries. Every year, there are 1.3 million new cases of CRC globally with a 5-year prevalence rate of 3.2 million. In India, though the incidence of CRC has increased marginally, it is now the fifth most common cause of cancer mortality among Indian men and women. In India, the annual incidence rates for colon cancer and rectal cancer in men are 4.4 and 4.1 per 100000, respectively and the annual incidence rate for colon cancer in women is 3.9 per 100000. Thus, colon cancer ranks $8^{th}$ and rectal cancer ranks $9^{th}$ among men while for women, rectal cancer does not figure in the top 10 cancers, whereas colon cancer ranks $9^{th}$.

Risk factors for CRC include age (risk of colorectal cancer increases with age), gender (25% higher in men than in women), personal history of colorectal polyposis, inflammatory bowel disease (Ulcerative colitis or Crohn's disease), family history of colorectal cancer and lifestyle related factors like obesity, alcohol consumption and cigarette smoking. Being physically inactive also increases the risk of developing colorectal cancer.

Signs of colorectal cancer are change in bowel habit, sensation of incomplete emptying after passing motion, blood mixed with stool, passing mucus with stool, sensation of fullness after eating is less, abdominal distension, abdominal pain, weight loss, constipation, diarrhea, frequent urge to pass stool, fatigue, vomiting, bloating and pain in the abdomen, iron deficiency and a lump in the stomach.

Surgery, chemotherapy, and radiotherapy are still the major conventional cancer therapies. However, more than 50% of patients have minimal or no benefit from these treatments and most of them suffer from their toxic adverse reactions. Alternative medicine (like herbal medicines) has become increasingly popular among cancer patients with a prevalence of its use as high as 80%.

Neem also known as *Azadirachta indica* is commonly found in many semi-tropical and tropical countries including India. The components extracted from neem plant have been used in traditional medicine for the cure of multiple diseases including cancer for centuries. Studies have shown compelling evidence suggesting that the anticancer effects of neem are mediated through modulation of multiple cellular processes. Nimbolide, an active molecule isolated from *Azadirachta indica*, has been reported to exhibit several medicinal properties. It has shown potent anticancer activity against several types of cancer and has demonstrated potential anti-cancer activity in several in-vivo and in-vitro studies. Nimbolide acts by generating reactive oxygen species (ROS), thereby inducing apoptosis, inhibition of metastasis and angiogenesis. Another component nimbin, a triterpenoid isolated from *Azadirachta indica* possess anti-inflammatory, anti-pyretic, anti-histamine and anti-fungal properties.

WO2015035199A1 patent provides a method for treating one or more symptoms of cancer by administering a therapeutically effective dose of a pharmaceutical formulation to the patient to ameliorate one or more symptoms of the cancer or to reduce the number of cancer cells, wherein the pharmaceutical formulation comprises Nimbolide; Nimbandiol; 2', 3' dihydro Nimbolide; 28 dihydro Nimbolide, or a combination thereof. The extract was examined on plasma and tumor tissues of mice at a dosage of 200 mg/kg of body weight administered orally. Targeted cancers were prostate cancer, colon cancer, astrocytoma and sarcoma. The invention provides bioactive compounds from Super Critical Neem Leaf Extract that exert anti-tumor activity. The patent claims the reduction of number of cancer cells, but the impact of reduction of cancer cells on symptoms of cancer is not known/determined/demonstrated. The extraction was carried out using supercritical $CO_2$ at a pressure of 632.76 $kg/cm^2$ and a temperature of 50° C. and collection was done at −49° C. using a dry ice/acetone bath. This huge difference between extraction temperature and separation temperature may cause unforeseen detrimental changes in the phytoconstituents. Also, the separation temperature is not commercially viable or scalable for industrial production.

CN101972246B provides an anti-tumor medicament which contains effective amount of *Azadirachta indica* triterpenoid 1 or 2 or 3 and a pharmaceutically acceptable carrier. It also provides a preparation method of a medicament which contains the compounds 1 to 3, and the application of the compounds to the preparation of medicaments for preventing and treating tumor diseases. It is provided to target leukemia, liver cancer, lung cancer and breast cancer. The extraction process was carried out by first subjecting herbs to methanol extraction and then subjecting the diluted methanolic extract to petroleum ether extraction and ethyl acetate extraction. The daily dosage varies from 0.01-10 mg/kg of body weight, with oral, parenteral, intrathecal or intraventricular administration.

CN103864876A relates to new triterpenoid xylocarpus granatum isolated from the neem tree fruit and use in the preparation of a medicine for malignant tumors particularly lung cancer and breast cancer. As stated in the patent application, pharmacological tests showed that the compound has inhibitory activity on the A-549 human lung adenocarcinoma cell line. Methanolic extract of neem tree foliage was used. It was also tested on human breast cancer cells A-549 for antitumor activity.

U.S. Pat. No. 5,370,873A relates to a purified extract of Azadirachta indica leaves which inhibit adhesion of cancer cells and malarial-infected erythrocytes to cultured endothelial cells. The purified extract also inhibits in-vitro vital development of human immunodeficiency virus (HIV), yellow fever virus and sandfly fever (Sicilian) virus and inhibits in titro development of both sexual (gametocytes) and asexual (schizonts) forms of human malarial parasites. It also relates to a process for extracting purified extract from Neem leaves by soxhlet extraction, by a variety of solvents such as alcohols, acetone, pyridine, water etc. followed by passive precipitation and HPLC fractionation. The mechanism of working as stated is that due to anti-adhesive property of the neem leaf extract, the extract renders the cancer cells and infectious cells ineffective and non-proliferative.

JP2009274956A provides a composition which contains Epoxyazadiradione, gedunin, 17-epi-17-hydroxyazadiradione and 7-O-benzoylnimbocinol as active components in Neem seed extract to target leukemia, lymphomas, skin cancer, lung cancer, colon cancer, stomach cancer, breast cancer, prostate cancer, epithelial cell cancers such as thyroid cancer, bone sarcoma, etc. The extracts were obtained by using n-hexane followed by methanol and the fractionation by using column chromatography. The cytotoxic activity is based on apoptosis inducing activity of the compounds in the Neem seed extract. Also, it possesses anti-tumor activity. The test compounds were added to DMSO at concentrations of $1 \times 10^{-4}$, $1 \times 10^{-5}$, $1 \times 10^{-6}$ M and its activity was tested. However, whether the effects are dose dependent, needs to be ascertained.

WO2007137389A1 provides a pharmaceutical composition for treatment of patients suffering with the human immunodeficiency virus. The composition can be administered orally. This composition comprises an effective amount of components obtained from Azadirachta indica, and a protein supplement. The composition is produced by immersing powder Neem in water to produce an aqueous extract.

From these patent art review, it was observed that, in conventional solvent extraction processes, the separation temperature is always greater than extraction temperature. The extraction of herb at higher temperature destroys or modifies molecular and chemical structure of temperature sensitive phytoconstituents which provide therapeutic value of herb. Also, it was seen from the art that the herb is extracted using solvents such as hexane, methanol, and acetone which are considered hazardous and carcinogenic for humans. Hence, there is a need for alternate but robust process for preparation of $CO_2$ extract of Azadirachta indica in order to protect the heat sensitive phytoconstituents during extraction process and thereby protect therapeutic value of herbal formulation that is required for treatment of cancers especially Oral and Colon cancers.

Thus, the objective of the present invention is to develop a robust process for obtaining Azadirachta indica leaf extract without compromising on the heat sensitive phytoconstituents.

SUMMARY OF THE PRESENT INVENTION

The present invention provides a process for preparing Azadirachta indica leaf extract by using supercritical carbon dioxide ($SCO_2$). The extract prepared can be administered either orally as capsules (veggie or hard gelatin capsules, liquid veggie capsules or soft gelatin capsules) or can be used as liquid mouthwash or sublingual oral formulation.

Various embodiments disclosed herein relate to a process for preparation of a $CO_2$ extract of Azadirachta indica leaves, by:
 a) powdering dried Azadirachta indica leaves having a moisture content of less than 12% to obtain a powder comprising particles having a size of less than 0.42 mm;
 b) subjecting the powder to extraction with supercritical $CO_2$ at a pressure ranging from 80 Bar (80 kg/cm) to 350 Bar (350 kg/cm) at a temperature ranging from 31° C. to 45° C. to obtain a $CO_2$ composition comprising $CO_2$ extractives and a residual powder, c) separating the $CO_2$ extractives from the $CO_2$ composition at a pressure ranging from 40 Bar to 65 Bar at a temperature lower than the extraction temperature to obtain an Extract A, e.g., a temperature of between 10° C. and 30° C.;

d) subjecting the residual powder to further extraction using a mixture of $CO_2$ and ethyl alcohol at a pressure ranging between 80 Bar to 350 Bar and at an extraction temperature ranging from 31° C. to 45° C. to obtain an ethyl alcohol/$CO_2$ composition comprising *Azadirachta indica* extractives;

e) recovering the *Azadirachta indica* extractives from the ethyl alcohol/$CO_2$ composition as an Extract B by reducing a solvent pressure to between 40 Bar and 65 Bar at a temperature lower than the extraction temperature, e.g., a temperature of between 10° C. and 30° C., followed by vacuum distillation of the ethyl alcohol; and f) combining the Extract A and the Extract B to obtain the $CO_2$ extract of *Azadirachta indica* leaves.

According to various embodiments, subjecting the powder comprising particles having a size of less than 0.42 mm to supercritical $CO_2$ extraction is carried out at a flow rate of 10 to 40 kg of $CO_2$ per kg of raw material.

According to various embodiments, the extract A may be passed through a high velocity micro-jet or nozzle to obtain particles having a particle size of between 10 nm and 100 nm.

According to various embodiments, the mixture of $CO_2$ and ethyl alcohol used when subjecting the residual powder to further extraction contains 3 to 10% of ethyl alcohol, based on the weight of the $CO_2$.

According to various embodiments, the vacuum distillation of ethyl alcohol is carried out at a temperature below 45° C.

According to various embodiments, the $CO_2$ extract of *Azadirachta indica* leaves obtained by combining Extract A and Extract B includes Nimbolide in a minimum amount of 3 mg/gm; Nimbin in a minimum amount of 130 μg/gm; and Salinin in a minimum amount of 200 μg/gm. In various embodiments, the $CO_2$ extract of *Azadirachta indica* leaves may further comprise a minor amount of Desacetylnimbin, Azadiradione, Azdirone, Nimbolin, Nimbinene, or a mixture thereof.

Various embodiments disclosed herein relate to a therapeutic herbal composition, including an effective amount of 50 to 300 mg of a $CO_2$ extract of *Azadirachta indica*, containing Nimbolide in a minimum amount of 3 mg/gm; Nimbin in a minimum amount of 130 μg/gm and Salinin in a minimum amount of 200 μg/gm; and one or more pharmaceutical carriers or excipients. The $CO_2$ extract of *Azadirachta indica* may also include a minor amount of at least one phytoconstituent selected from the group consisting of Desacetylnimbin, Azadiradione, Azdirone, Nimbolin, and Nimbinene. In various embodiments, the therapeutic herbal composition may be used in an oral dosage form.

In a preferred aspect, the invention provides a process of preparing *Azadirachta indica* leaves extract containing beneficial phytoconstituents. The process involved following steps:

Drying clean and matured *Azadirachta indica* leaves to reduce moisture to less than 12%, followed by powdering the dried leaves to obtain powder with particles having a size below 0.42 mm;

Subjecting the powder particles to supercritical $CO_2$ extraction at a pressure varying between 80 Bar (80 kg/cm) and 350 Bar (350 kg/cm) at a temperature ranging between 31° C. to 45° C.; at a flow rate of 10 to 40 kg of $CO_2$ per kg of raw material; and Separating a $CO_2$ extract from the powder, while maintaining pressure varying between 40 Bar to 65 Bar and temperature between 10° C. to 30° C. to obtain Extract A.

The remaining residual powder after separating Extract A is subjected to further extraction using a mixture of $CO_2$ and ethyl alcohol at a pressure ranging between 80 Bar to 350 Bar and temperature ranging between 31° C. to 45° C.; and an ethyl alcohol/$CO_2$ extract composition is collected from the separator by reducing the solvent pressure to between 40 Bar and 65 Bar and reducing the temperature to between 10° C. to 30° C., followed by vacuum distillation of ethanol to obtain Extract B.

Extract A and Extract B are combined to obtain an Extract C, described herein as a $CO_2$ extract of *Azadirachta indica* leaves.

In another aspect, the Extract A is subjected to extremely high velocity and passed through a micro-jet or nozzle to obtain fine a sized nano particle extract. Nano sized delivery technologies are currently in use for sustained and enhanced delivery of active phytoconstituents. By subjecting the Extract A to a high velocity micro-jet, a minimum 10% of the Extract A is obtained with a particle size between 10 and 100 nm. Hence the extract obtained by this process is considered as "Supercritical Neem Leaf Extract-Nano 10%".

The *Azadirachta indica* leaves are extracted using supercritical $CO_2$ extraction ($SCO_2$) and under specific temperature & pressure conditions to ensure that the extract contains no harmful extraction solvents and retains all beneficiary ingredients.

Thus, supercritical $CO_2$ extraction ($SCO_2$) which is used in the present invention with or without entrained ethanol does not leave any hazardous solvent residues. The extraction temperature is maintained between 31° C. to 45° C., which ensures the retention of all temperature sensitive ingredients.

The method adopted by the present inventors for extraction ($SCO_2$ extraction with or without entrained ethanol) has a much lower separation temperature than the extraction temperature. The typical temperature for extraction is 31 to 45° C. while the separation temperature is around 10° C. to 30° C. in the present process. Thus, integrity of phytoconstituents is maintained along with retention of the temperature sensitive ingredients. Also, the extraction pressure is much lesser than the pressure used in the prior art (WO '199), which further ensures the retention of sensitive phytoconstituents, and thus the $SCO_2$ extract of the present invention comprises the active components which are different from the disclosures of WO'199.

In a further embodiment, the $CO_2$ extract thus obtained was standardized by HPLC analysis using C18 column (4.6 mm×250 mm×5 m) and results were monitored at 215 nm using UV detection. The sample was prepared in Methanol and the mobile phase was Methanol and water. A gradient program sequence was used at a flow rate of 1 ml/min.

Accordingly, in another aspect, the present invention provides a standardized $SCO_2$ extract which comprises Nimbolide in a minimum amount of 3 mg/gm; Nimbin in a minimum amount of 130 μg/gm and Salinin in a minimum amount of 200 μg/gm to ensure the therapeutic efficacy of the extract when administered as the herbal formulation. The $CO_2$ standardized extract also contain various other active phytoconstituents such as Desacetylnimbin, Azadiradione, Azdirone, Nimbolin, and Nimbinene which may be contributing to this activity. However, the same are not quantified as they are in lesser quantities.

Based on the minimum concentrations of Nimbolide, Nimbin and Salinin in the standardized extract as mentioned above in-vitro experiments were carried out using the standardized supercritical neem extract (SCNE) in human oral and colon cancer cell-lines. These experiments demonstrated that the standardized $CO_2$ extract possesses anti-proliferative activity, suppresses cancer growth and induces apoptosis through the pro-inflammatory pathway and NF-kB inhibition.

Accordingly, in another aspect, the invention provides herbal compositions for oral application comprising of standardized $SCO_2$ extract of Azadirachta indica leaves in an effective amount along with one or more pharmaceutical carriers/excipients that exerts very good antitumor activity against Oral and Colon cancers.

DESCRIPTION OF DRAWINGS

The patent or application file contains at least one drawing executed in color. Copies of this patent or patent application publication with color drawing(s) will be provided by the Office upon request and payment of the necessary fee.

In order to better understand various exemplary embodiments, reference is made to the accompanying drawings, wherein.

DETAILED DESCRIPTION

In accordance with the above aspects, the invention will now be described in detail in connection with certain preferred and optional embodiments, so that various aspects thereof may be more fully understood and appreciated.

Azadirachta indica known as Neem is a fast-growing evergreen tree which belongs to family Meliaceae. The extracts of seeds, leaves, flowers, stem, bark and fruits of neem have consistently been used as medicine in various diseases. It is native to tropical and sub-tropical parts of India including Andhra Pradesh, Tamil Nadu and Karnataka and is also found in south-east Asia. It is also widespread in West Africa, the Caribbean and South and Central America.

The dried Azadirachta indica leaves are sourced from states of Rajastan and Madhaypradesh, India.

In this invention $CO_2$ extract derived from dried leaves of the plant is used for therapeutic application.

Accordingly, in a preferred aspect, the invention provides a process of preparing standardized $CO_2$ extract of Azadirachta indica leaves containing beneficial phytoconstituents. The process involved following steps:

Powdering the clean and matured dried Azadirachta indica leaves having moisture to less than 12% to obtain powder with fine particles of size below 0.42 mm;

subjecting the powder to supercritical $CO_2$ extraction at a pressure varying between 80 Bar (80 kg/cm) and 350 Bar (350 kg/cm) at a temperature ranging between 31° C. to 45° C.; at a flow rate of 10 to 40 kg of $CO_2$ per kg of raw material;

Separating $CO_2$ extractives maintaining pressure varying between 40 Bar to 65 Bar and at a temperature lower than the extraction temperature to obtain Extract A;

Subjecting the remaining residual powder after separating Extract 'A' to further extraction using mixture of $CO_2$ and ethyl alcohol at the pressure ranging between 80 Bar to 350 Bar and temperature ranging between 31° C. to 45° C.;

Collecting Ethyl alcohol laced with $CO_2$ extract from separator by reducing the solvent pressure between 40 Bar and 65 Bar and at a temperature lower than the extraction temperature, followed by vacuum distillation of ethanol to obtain Extract B; and Combining Extract A and Extract B to obtain Extract C which is called as $CO_2$ standardized extract of Azadirachta indica leaves.

The matured leaves of Azadirachta indica considered for extraction are preferably of the same age.

The size of the dried powdered particles is below 0.42 mm.

The separation temperature in step c) and collection temperature in step e) is maintained between 10° C. to 30° C.

The vacuum distillation of ethanol is carried at temperature below 45° C.

The ethyl alcohol used in step d) is in an amount of 3 to 10% of the $CO_2$.

The time required for $CO_2$ extraction depends upon the size of the extractors and the quantity of herb loaded into the extractor at a time. The quantity of $CO_2$ to be pumped through the herb varies between 10 kg of $CO_2$/kg of herb to 40 kg of $CO_2$/kg of herb depending upon the solubility of lipophilic compounds present in the herb. $CO_2$ carries the extractives to the separator where the pressure of $CO_2$ is reduced to a pressure varying between 40 Bar to 65 Bar and the temperature is in the range of 10° C. to 30° C. as required to separate the solute (extract) and the $CO_2$.

This method of extraction is known as Supercritical $CO_2$ extraction, which is the safest method of extraction for dried herbs. The extract thus obtained contains all the temperature sensitive major and minor ingredients present in the herb and all the other lipophilic soluble compounds. In the present invention the extract thus obtained is called as Extract A.

The remaining residual powder after isolating Extract 'A' is further subjected to extraction using mixture of $CO_2$ and ethyl alcohol in proportion of 90 to 97% of Supercritical $CO_2$ and 3 to 10% of ethyl alcohol. The extraction was carried out at the pressure ranging between 80 Bar and 350 Bar and temperature ranging between 31° C. to 45° C. The quantity of solvent pumped ($CO_2$+Ethanol) varies between 10 kg/kg of herbs to 40 kg/kg of herbs. The solute (extract) and ethanol were separated from the $CO_2$ on reducing the solvent pressure between 40 Bar and 65 Bar and temperature between 10° C. to 30° C. The mixture of ethyl alcohol laced with $CO_2$ extract was collected from the separator and then subjected to vacuum distillation for separating the ethyl alcohol completely from the solute (extract). This extract is known as Extract B.

Finally, both the extracts (Extract A and Extract B) were combined to obtain Extract C. This combined extract is termed as $SCO_2$ extract of *Azadirachta indica* leaves, as described in the following examples.

In another aspect, the Extract A is subjected to extremely high velocity and passed through a micro-jet or nozzle, then fine sized nano particle extract is obtained. Nano sized delivery technologies are known to potentially improve effect of the formulation. Minimum 10% of the extract is obtained with particle size between 10-100 nm. Hence the extract obtained in this aspect is considered as "Supercritical Neem Leaf Extract-Nano 10%". Accordingly, this "Supercritical Neem Leaf Extract-Nano 10%" may be combined with extract B to obtain extract C.

The yield of the $CO_2$ extract may be anywhere in the range of 2.5% to 5% w/w.

The supercritical $CO_2$ extraction (SCO) which is used in the present invention with or without entrained ethanol does not leave any hazardous solvent residues. The extraction temperature is maintained between 31° C. to 45° C., which ensures the retention of all temperature sensitive ingredients. Also, the extraction pressure is much lesser than the pressure of the process reported in WO'199.

The method adopted by the present inventors for extraction ($SCO_2$ extraction with or without entrained ethanol) always has a much lower separation temperature than the extraction temperature. Extraction at lower temperature reduces the risk of damage to thermolabile compounds. Thus, integrity of phytoconstituents in the present invention is maintained apart from retaining the temperature sensitive ingredients. The typical temperature for SCF (Super Critical Fluid) extraction of the present invention is 31 to 45° C. while the separation temperature will be around 10° C. to 30° C.

The additional advantage of the present invention vis-à-vis the process reported in WO2015035199 is that the process can be achieved at much less pressure compared to the pressure of the process reported in WO'199. Moreover, the yields of the reported process in WO'199 are approximately 5%. The formulation may contain certain amount of impurities as higher extraction pressures can result in extraction of waxes and resins which remained as impurities. On the contrary, composition prepared as described in the present disclosure have lower levels of impurities, as extraction is carried out at lower pressure allowing the selective extraction of active compounds.

In another embodiment, the herbal powder of *Azadirachta indica* leaves was subjected to water extraction to obtain the water-soluble extractives in a paste form. The extract thus obtained was dried in tray dryers/vacuum dryer or in spray drier to obtain free flowing powder extract. This extract is termed water extract in one of the examples (example 3).

In another aspect, the present invention provides standardized $SCO_2$ Neem extract (SCNE) which comprises Nimbolide in a minimum amount of 3 mg/gm; Nimbin in a minimum amount of 130 µg/gm and Salinin in a minimum amount of 200 µg/gm to ensure the maximum therapeutic efficacy of the extract when administered as herbal formulation. The $CO_2$ standardized extract also contain various other active phytoconstituents such as Desacetylnimbin, Azadiradione, Azdirone, Nimbolin, and Nimbinene which may be contributing to this activity. However, the same are not quantified as they are in smaller quantities.

Accordingly, in another aspect, the invention provides therapeutic herbal compositions for oral application comprising of standardized $SCO_2$ extract of *Azadirachta indica* leaves in an effective amount of 50 to 300 mg along with one or more pharmaceutical carriers or excipients that exerts antitumor activity against Oral cancer and Colon cancer.

The pharmaceutical excipients/carriers are selected from the group consisting of distilled water, saline, aqueous glucose solution, alcohol (e.g. ethanol), surfactants, propylene glycol, tween-80 and polyethylene glycol; and oily carriers such as various animal and vegetable oils, white soft paraffin, paraffin, wax, glucose, fructose, sucrose, maltose, yellow dextrin, malt dextrin, white dextrin, aerosol, aerated or fumed silica, di-calcium phosphate, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol Rosemary (*Rosemarinus officinalis*) $CO_2$ extract, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, aerated or fumed silica, calcium salts, pigments, flavors and preservatives.

In a preferred embodiment, extract used in the formulation is made using $SCO_2$ extraction with or without entrained solvent ethanol, using the below mentioned conditions.

Pressure of extraction: Between 72 kg/cm² to 550 kg/cm²
Preferred Range: 80 kg/cm² to 350 kg/cm²
Entrained ethanol: 0-10% (Preferred range 3 to 7%)

In general, the herbs are extracted using conventional methods using conventional solvents such as cold pressing method, conventional extruder press method, solvent extraction, distillation "modified atmosphere packing" (MAP).

Supercritical $CO_2$ extraction is a process that produces an extract with a broad spectrum of the non-polar lipophilic constituent compounds present in the herb such as oils, fatty acids along with vital temperature sensitive phytonutrients. The spectrum of the extractives can be widened by using up to 10% of ethanol as an entrained solvent along with pure $CO_2$. The major advantages of using this process of extraction are retention of all the temperature sensitive ingredients present in the herb which contributes toward health benefits. Unlike other solvent extraction methods where solvents such as Hexane, Chloroform, Acetone which are hazardous are used, the present extract is free of hazardous solvent residues as well as heavy metals contamination. Heavy metals are below the detectable limit in the present extract as $CO_2$ is a highly non-polar solvent and heavy metals are highly polar, and hence they are not soluble in $CO_2$.

When ethanol is used as entrained solvent the resulting extract is obtained by removing the ethanol from the extract to the extent under vacuum (27 to 28.5 inch of Hg) keeping temperature below 45° C., so that the residual solvent (ethanol) remains less than 1000 ppm and hence can be used safely for making the formulation.

The extract used in the present invention was also reduced to nanoparticles, to a size between 10 nm-100 nm, by using extremely high velocity and passing through a micro-jet or nozzle. The particles were characterized by using Dynamic Light Scattering (DLS). DLS is a light scattering technique.

The basic principle of DLS is that the sample is illuminated by a laser beam and the fluctuations of the scattered light are detected at a known scattering angle by a fast photon detector. Analysis of the fluctuation of the scattered light yields information about the particles.

The SCNE thus obtained was subjected to HPLC and LC-MS to identify signature of triterpenoids with potential cancer preventive activity. Accordingly, in an additional aspect, the $SCO_2$ Neem extract thus obtained is characterized to have minimum concentrations of Nimbolide in an amount of 3 mg/gm; Nimbin in an amount of 130 µg/gm and Salinin in an amount of 200 µg/gm so as to ensure the efficacy of the extract prepared in the present invention.

In a further embodiment, the invention provides compositions comprising a therapeutically effective amount of a supercritical $CO_2$ neem extract (SCNE) which is characterized to comprise nimbolide, nimbin and salinin. The concentrations of any of the nimbolide, nimbin and salinin can vary in the SCNE of the present invention. However, in some aspects, the SCNE can comprise at least 3 mg/g nimbolide. In some other aspects, the SCNE can comprise at least 130 µg/g nimbin. In yet another aspect, the SCNE can comprise at least 200 µg/g salinin.

In some of the aspects, the amount of the nimbolide present in the composition can be at least 3 mg/g; the amount of the nimbin present in the composition can be at least 130 µg/g nimbin; and the salinin present in the composition can be at least 200 µg/g.

In some other aspects, the composition can further comprise a pharmaceutically acceptable excipient.

Accordingly, in a further embodiment, the invention provides herbal pharmaceutical compositions which comprises; physiologically effective amount of the standardized (SCNE) extract with above minimum concentration of Nimbolide; Nimbin and Salinin; or a combination thereof, in a pharmaceutical carrier/excipient to inhibit at least one of the markers of proliferation, apoptosis, and anti-cancer activity of the Oral and Colon cancers. The physiologically effective amount of the extract is in the range of 50 to 300 mg per day. This minimum concentration of Nimbolide, Nimbin and Salinin or combination thereof are being achieved in the resultant $SCO_2$ extract by using the process disclosed in this application.

The compositions can be formulated into oral solid or liquid dosage forms.

Accordingly, the therapeutically effective formulations for oral use are prepared for example, in three ways to demonstrate the present invention.

In one exemplary embodiment, the first therapeutically effective formulation for oral use contains $SCO_2$ Azadirachta indica leaf extract. 75 mg (with minimum 0.22 mg Nimbolide; 9.75 µg Nimbin and Salinin 15 µg); naturally occurring antioxidants such as Vitamin E (tocopherols) or Rosemary (Rosemarinus officinalis) $CO_2$ extract containing minimum 6% Camosic acid: 10 mg and Sesame oil: 415 mg; or other naturally occurring oils as a carrier. Any other suitable antioxidants can be used in place of Vitamin E or Rosemary $CO_2$ extract. This formulation was provided as a soft gel capsule of 500 mg. The capsule can be administered to the patient 2-4 times a day (total 150-300 mg of Neem leaf extract per day as an active drug).

In another exemplary embodiment, the second therapeutically effective formulation for oral use contains $SCO_2$ Azadirachta indica leaf extract: 50 mg (with minimum 0.15 mg Nimbolide; 6.5 µg Nimbin and Salinin 10 µg), 582 mg dextrin/maltodextrin or other naturally occurring carrier (e.g. di-calcium phosphate or any other suitable pharmaceutical grade carrier); and 18 mg aerated or fumed silica. A free-flowing powder was prepared and encapsulated in suitable size hard gelatin or vegetarian capsule available in the market. The same can be administered 3-6 times a day to get a therapeutic dose of 150-300 mg Neem leaf $CO_2$ extract as described above.

In yet another embodiment, the third therapeutically effective formulation for oral use contains $SCO_2$ Azadirachta indica leaf extract: 50 mg (with minimum 0.156 mg Nimbolide; 6.5 µg Nimbin and Salinin 10 µg), 582 mg of water extract obtained from Neem leaf and 18 mg aerated or fumed silica. A free-flowing powder was prepared and encapsulated in suitable size of hard gelatin or vegetarian capsule available in the market. The same can be administered 3-6 times a day to get a therapeutic dose of 150-300 mg Neem leaf $CO_2$ extract as described above.

In another embodiment, a fine sized nano-particle $CO_2$ extract prepared by increasing velocity and passing the particle through micro-jet or nozzle, can be administered 2 to 3 times a day to get a therapeutic dose of 100 mg Neem leaf $CO_2$ extract nanoparticle as described above, instead of 150-300 mg of ordinary $CO_2$ extract.

In another preferred embodiment, the invention provides the composition in the form of a dietary supplement or an herbal medicine in conventional forms of Soft Gel Capsules, Hard Gel Capsules, Liquid Capsules, with or without carrier, dietary powders, drinks, substantially homogeneous mixture i.e., active ingredients are distributed evenly. In another preferred embodiment the invention provides a pharmaceutical composition for a mouthwash which contains 4.55% of $SCO_2$ Azadirachta indica leaf extract with standard carriers and additives like Sorbitol, Glycerin, emulsifiers, water and suitable flavors like mint, fruits, etc., A liquid formulation was prepared. The same can be administered 3 times a day, 20 ml each time, to get a therapeutic dose of 15 mg Neem Leaf $CO_2$ extract as described above. The mouthwash formulation is meant for use only in cases of oral cancer.

The compositions containing $SCO_2$ Azadirachta indica leaf extract can be administered in a dosage range of 50 mg to 300 mg per dose in any of the above-mentioned dosage forms. The recommended dose of administration is twice a day or thrice a day or two caps twice a day.

In yet another embodiment, the effect of SCNE was evaluated for oral and colon cancer by measuring cell viability (by MTT assay), DNA fragmentation by TUNEL assay [Terminal deoxynucleotidyl transferase dUTP nick end labeling], DNA condensation analysis with DAPI staining, measurement of apoptotic markers (intrinsic pathway: Bax, Bcl-2) protein by Western blot analysis and Flow cytometry to study the effect of SCNE on the cell cycle and the following conclusions are drawn.

Figure 2:
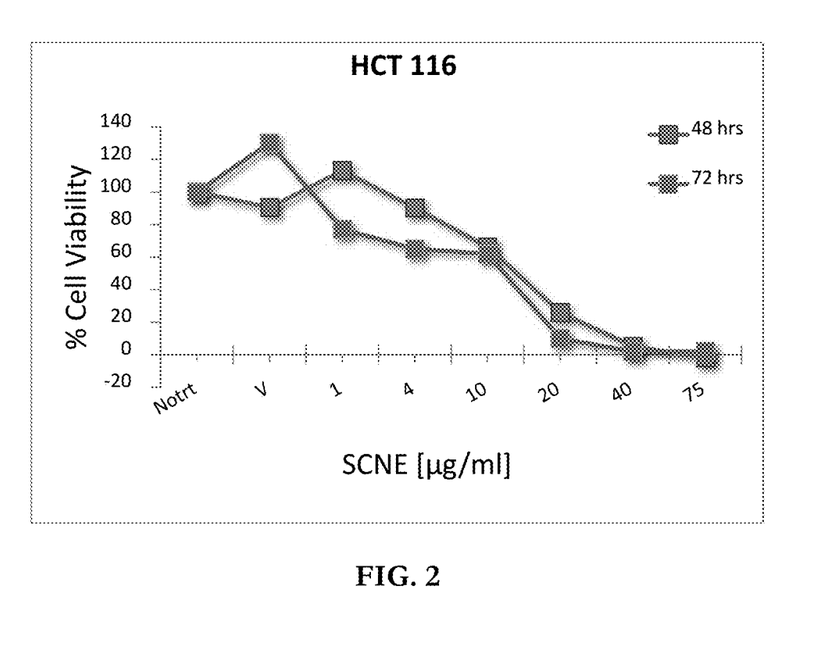
FIG. 2 shows the dose and time dependent effect of SCNE on cell viability in HCT 116 cells.
Figure 3:
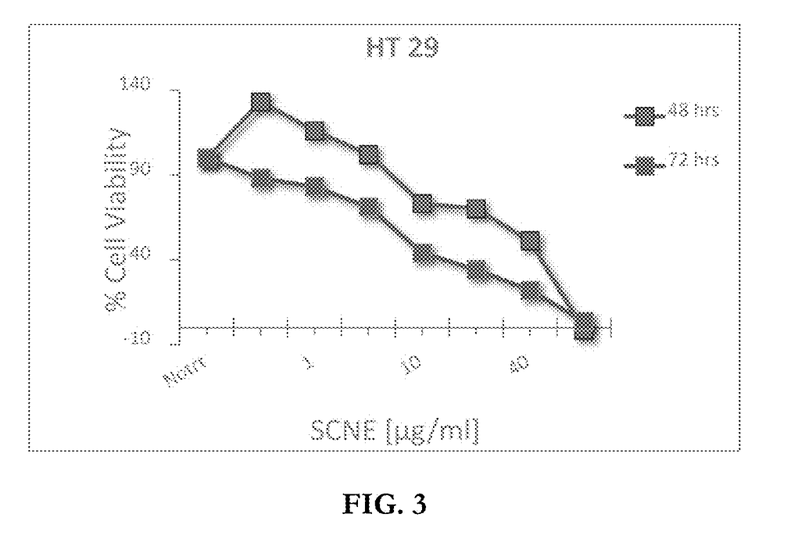
FIG. 3 shows the dose and time dependent effect of SCNE on cell viability in HT 29 cells.

SCNE impacts the viability of colon cancer cells in a time & dose dependent manner (FIGS. 2 to 3).

Figure 6:
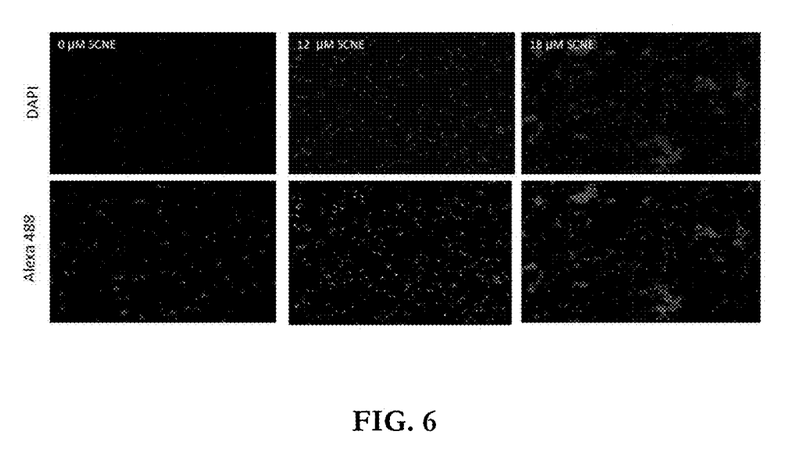
FIG. 6 shows that SCNE induces apoptosis in human colon cancer cells. HCT 116 cells were treated with varying concentration of SCNE for 72 h and DNA fragmentations were analyzed by detecting Alexa488 signal intensity.

SCNE induces apoptosis in human colon cancer cells. HCT 116 cells were treated with varying concentration of SCNE for 72 h and DNA fragmentations were analyzed by detecting Alexa488 signal intensity (FIG. 6).

Figure 7:
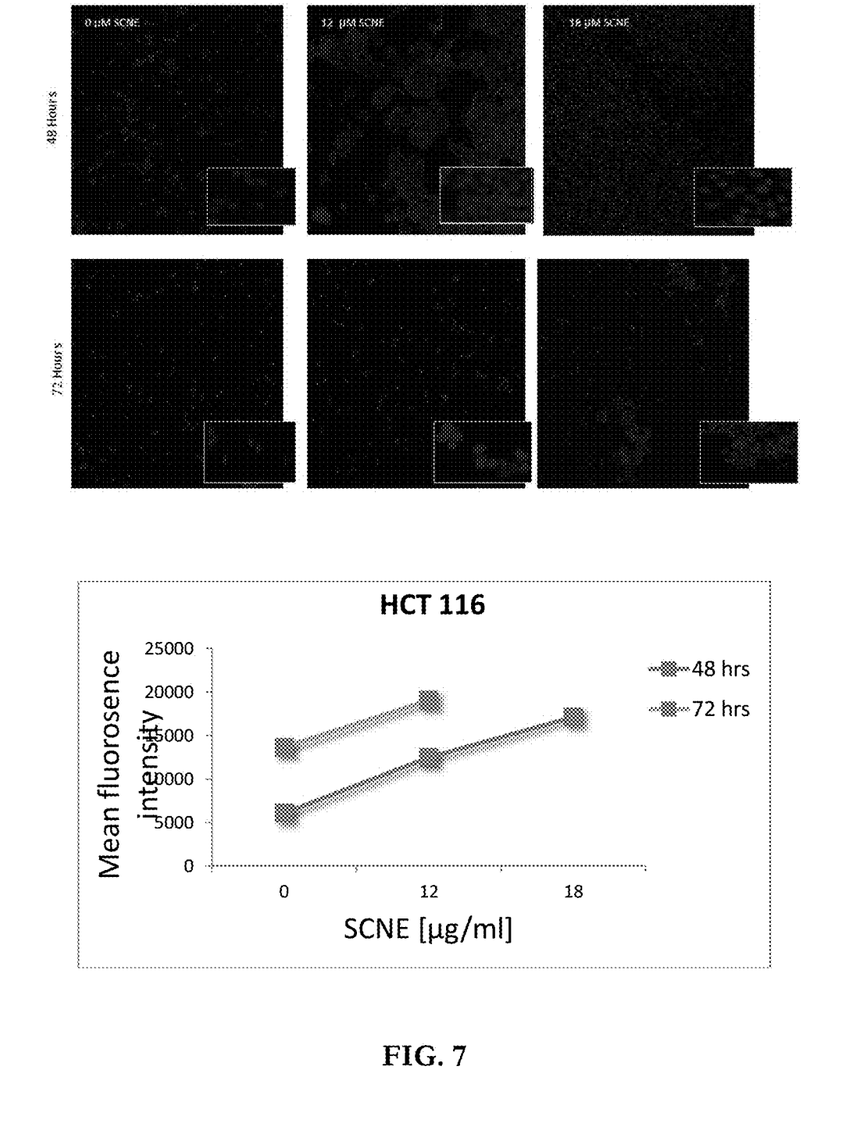
FIG. 7 shows that SCNE increases DNA condensation in human colon cancer cells. HCT 116 cells were treated with (0-18 μg/ml) SCNE for 48 h and 72 h. Nuclei are stained blue with DAPI.

SCNE caused increase in DNA fragmentation. This was consistent with the profound increase in DNA condensation observed in FIG. 7.

Figure 8:
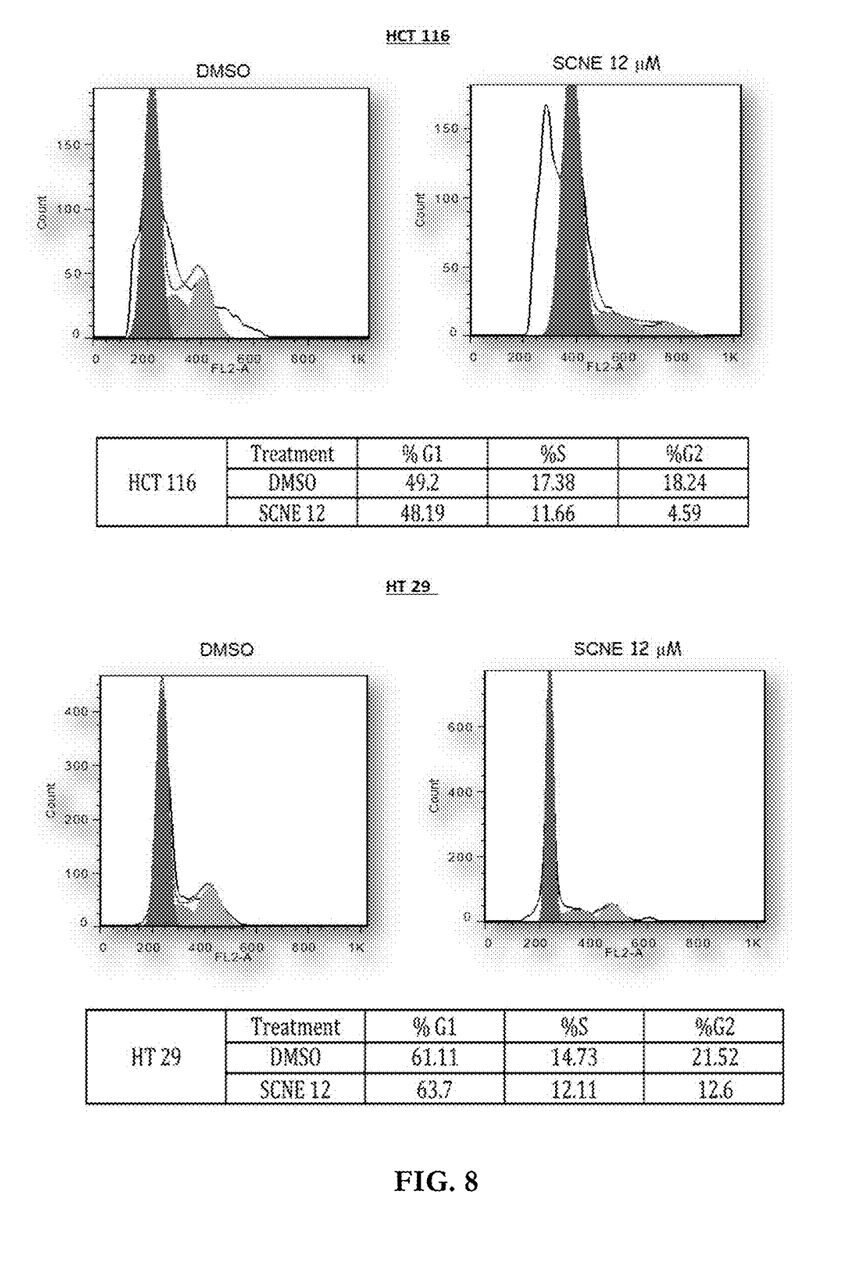
FIG. 8 shows the effect of SCNE on the cell cycle in human colon cancer cells.

Cell cycle analysis by flow cytometry confirmed a pre-apoptotic peak in SCNE treated HCT 116 cells for 48 h at IC50 (FIG. 8).

Figure 9:
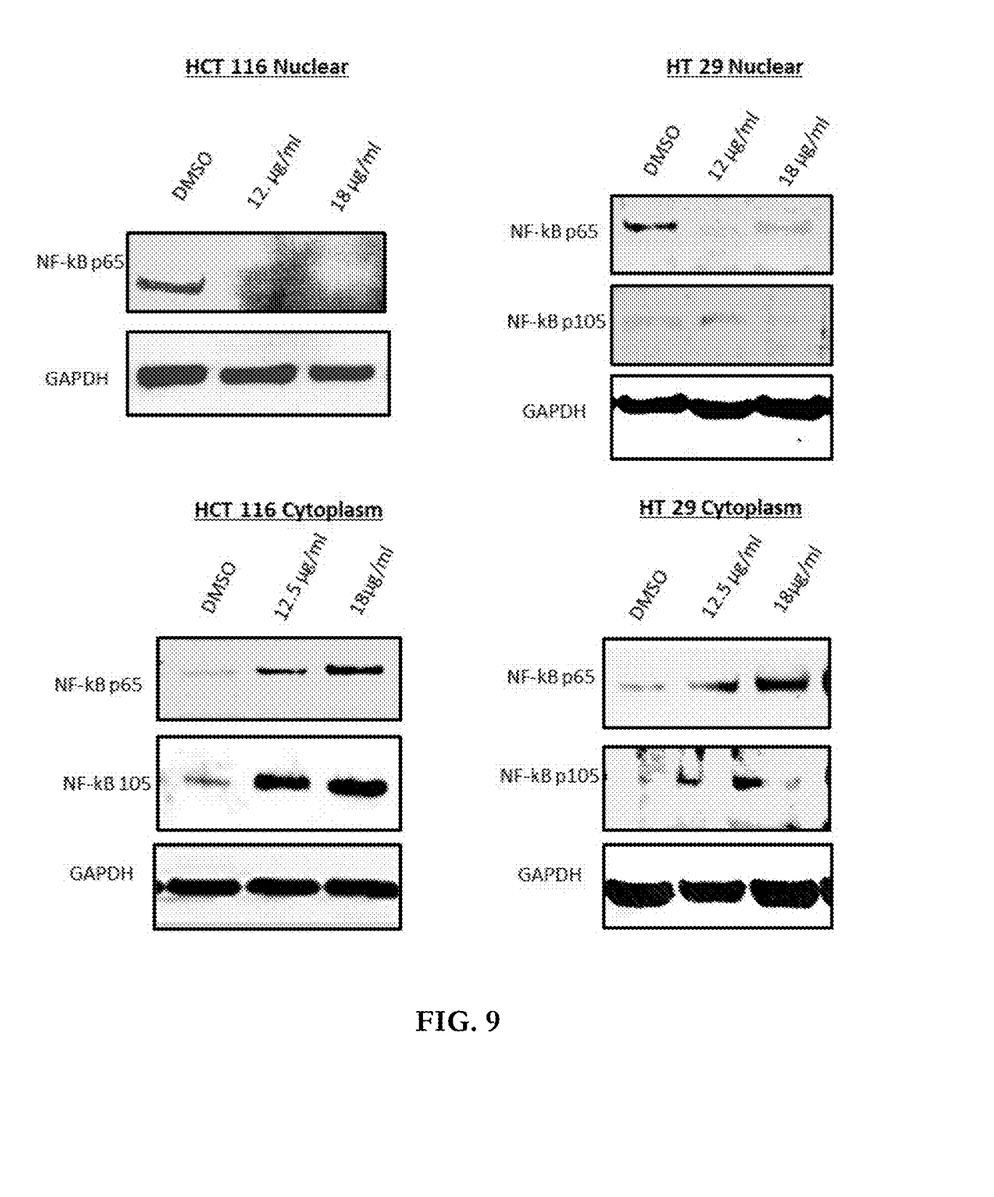
FIG. 9 shows that SCNE inhibits NF-kB translocation to the nucleus in human colon cancer cells.

SCNE treatment inhibited NF-kB translocation to the nucleus (FIG. 9).

Figure 10:
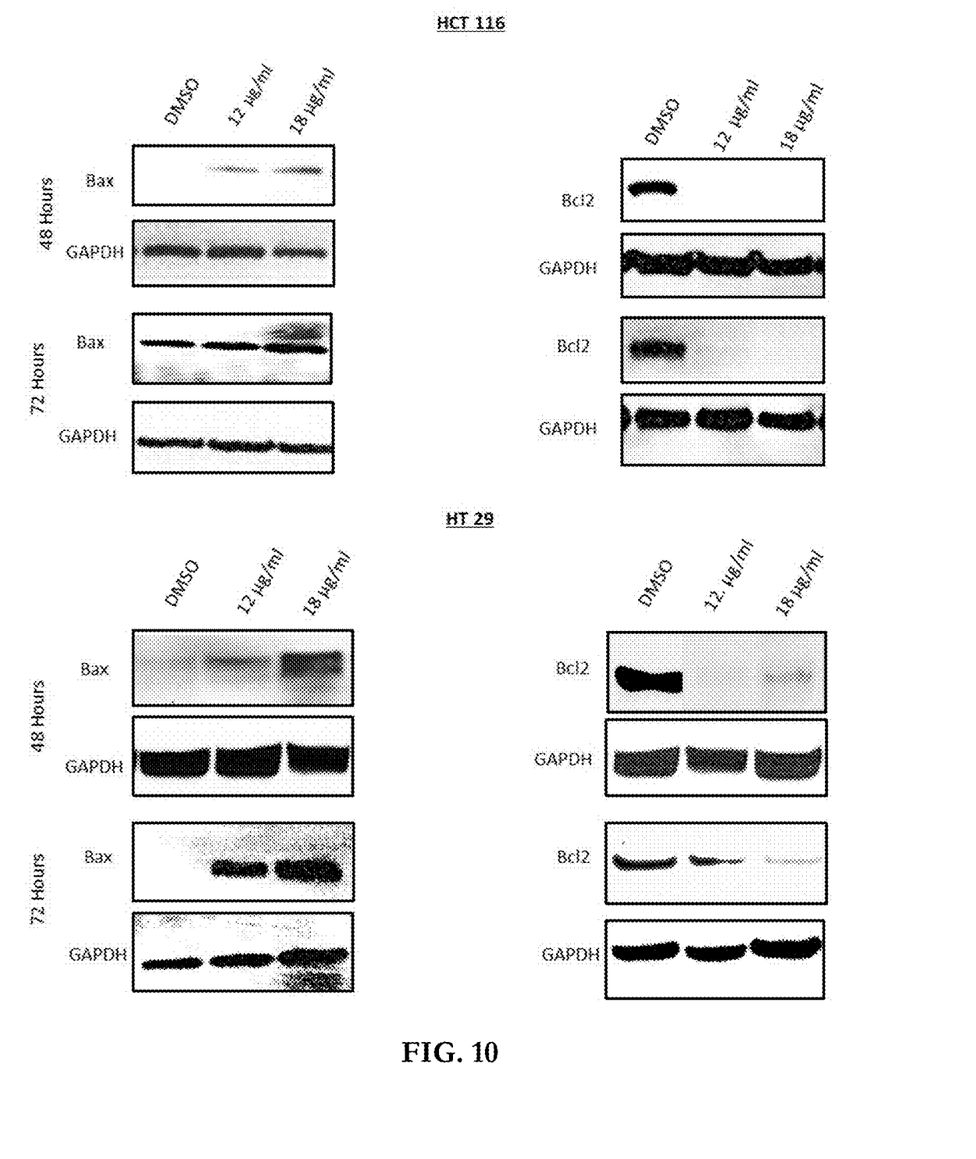
FIG. 10 shows that SCNE induces apoptosis in colon cancer cells. HCT116 and HT 29 cells were treated with (12-18 μg/ml) SCNE for 48 and 72 h.

SCNE increased the pro-apoptotic protein Bax, and decreased the anti-apoptotic protein Bcl2 (FIG. 10).

Accordingly, in an additional embodiment, the cancer preventive effect of a super critical $CO_2$ Neem extract of leaf (SCNE) and nimbolide alone was investigated on two human colon cancer cell lines, HCT 116 and HT 29. Normal Rat Colon cells IEC-6 cells also included in the study to verify the cytotoxicity of the SCNE extract. The effect of SCNE on cell viability was compared with nimbolide and the results are discussed below.

Figure 1:
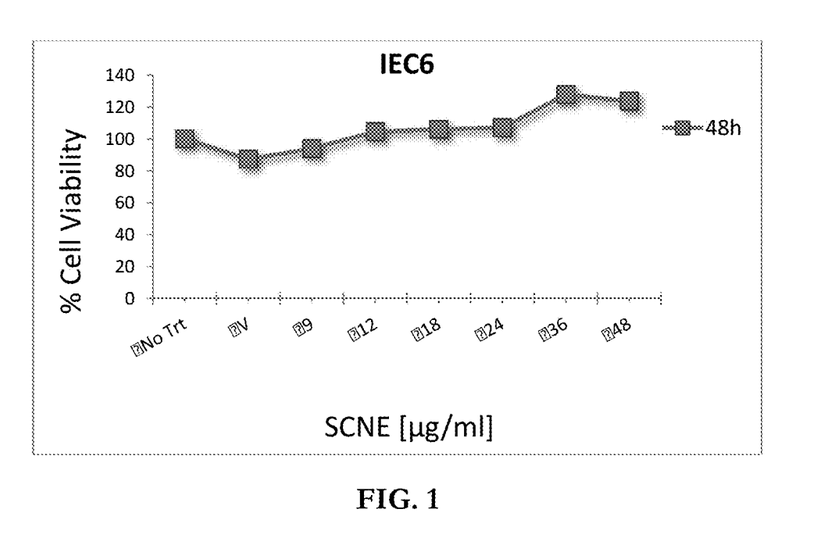
FIG. 1 shows the dose and time dependent effect of SCNE on cell viability in normal IEC6 cells.
Figure 4:
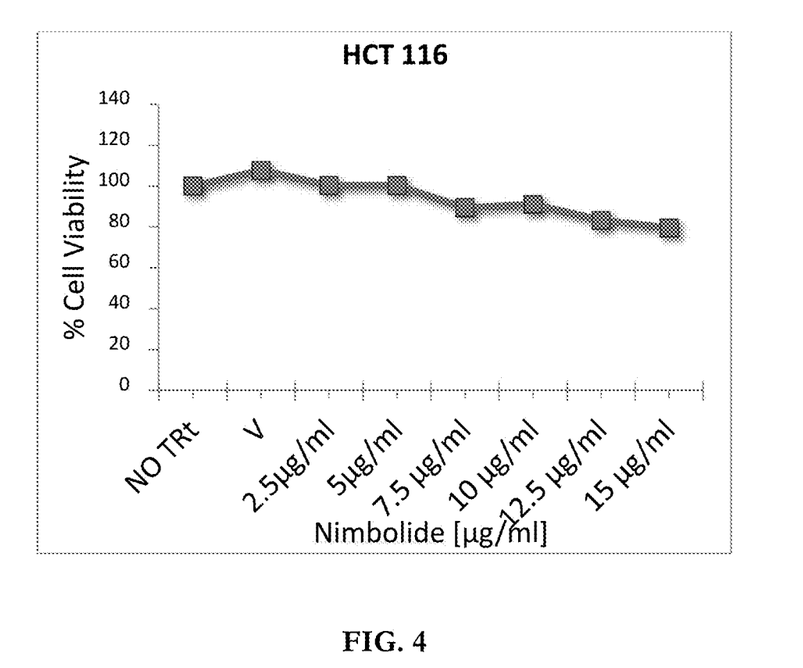
FIG. 4 shows the dose and time dependent effect of Nimbolide on cell viability in HCT 116 cells.
Figure 5:
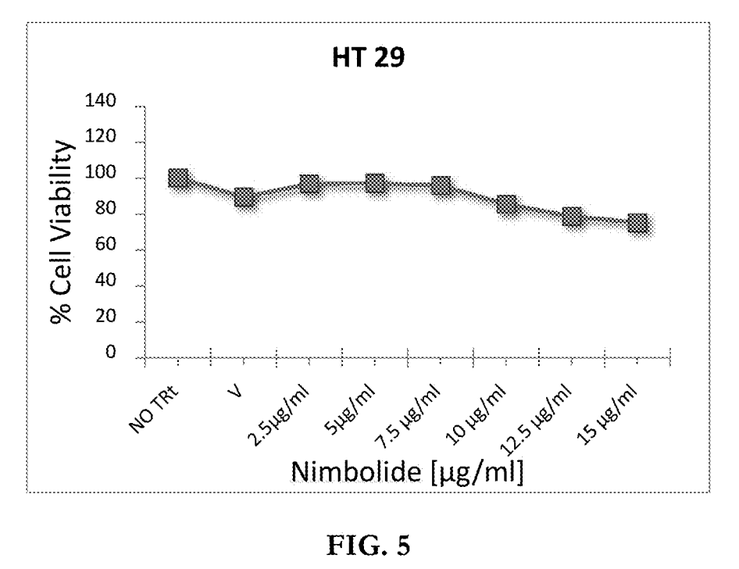
FIG. 5 shows the dose and time dependent effect of Nimbolide on cell viability in HT 29 cells.

The results confirm that the SCNE is non-toxic to normal Rat Colon cells IEC-6 cells even at higher concentration of 50 μg/mL after 48 hrs (FIG. 1). The SCNE treated colorectal cancer cells, viz., HCT116 and HT29 exhibits 62% (FIG. 2) and 44% cell viability (FIG. 3) respectively at a concentration of 15 μg/mL at the end of 72 hrs and exhibits zero cell viability at a concentration of 40 μg/mL (FIG. 2) and 75 μg/mL (FIG. 3) at the end of 48 and 72 hrs respectively. However, nimbolide treated colorectal cancer cells, viz., HCT116 (FIG. 4) and HT29 (FIG. 5) exhibits 80% and 75% cell viability respectively at a concentration of 15 μg/mL at the end of 48 hrs.

The above experiment conclusively confirmed that the super critical $CO_2$ neem leaf extract (SCNE extract) comprising a combination of Nimbolide, Nimbin and Salinin possess higher therapeutic efficacy than the nimbolide alone.

The following examples, which include preferred embodiments, will serve to illustrate the practice of this invention, it being understood that the particulars shown are by way of examples and for purpose of illustrative discussion of preferred embodiments of the invention.

Example 1

$CO_2$ Leaf Extract of *Azadirachta indica*

One KG of cleaned and matured *Azadirachta indica* leaves were taken and dried under the shade to reduce moisture content to less than 12%/o. It was ensured that the powder contains moisture less than 12%. Such dried herb was powdered in particle size below 0.42 mm and then subjected to $SCO_2$ extraction at a pressure varying between 80 Bar (80 kg/cm$^2$) and 350 Bar (350 kg/cm$^2$) at a temperature ranging between 31° C. and 45° C. The $CO_2$ was passed through the herb for a period of 2-3 hours depending upon the size of the extractors and the quantity of herb loaded into the extractor at a time. The quantity of $CO_2$ to be pumped through the herb varies between 10 kg of $CO_2$/kg of herb to 40 kg of $CO_2$/kg of herb depending upon the solubility of lipophilic compounds present in the herb. The $CO_2$ carried extractives were collected from the separator where the pressure of $CO_2$ was reduced to a pressure varying between 40 Bar to 65 Bar and temperature between 10° C. to 30° C. to separate the solute (extract) and the $CO_2$. The extract thus obtained contains all the temperature sensitive ingredients present in the herb and all the other lipophilic soluble compounds. The extract thus obtained is Extract A.

Residual powder after isolating Extract 'A' was subjected to extraction using mixture of $CO_2$ and ethyl alcohol in proportion of 90 to 97% of Supercritical $CO_2$ and 3 to 10% of ethyl alcohol. The extraction was carried out at the pressure ranging between 80 Bar and 300 Bar and temperature ranging between 31° C. to 45° C. The quantity of solvent pumped ($CO_2$+Ethanol) varies between 10 kg/kg of herbs to 40 kg/kg of herbs. The solute (extract) and ethanol were separated from the $CO_2$ on reducing the solvent pressure between 40 Bar and 65 Bar and temperature between 10° C. to 30° C. The ethyl alcohol laced with extract was collected from the separator. The mixture was then subjected to vacuum distillation (27 to 28.5 inch of Hg) keeping temperature below 45° C., for separating the ethyl alcohol completely from the solute (extract), which was named as Extract B.

Residual solvent (ethanol): less than 1000 ppm

Both the extracts extract 'A' and extract 'B' were combined to obtain Extract C.

Yield: 2.5-5%

Example 2

Water Extract of *Azadirachta indica*

The herb powder of *Azadirachta indica* leaves (1 KG) was subjected to water extraction to obtain the water-soluble extractives in a paste form. The extract thus obtained was dried in tray dryers/vacuum dryer or in spray dryer to obtain free flowing powder extract. This extract is termed as water extract.

Yield: 5:1%

Example 3

Standardization of the $CO_2$ Extract:

The standardization of the $CO_2$ extract was carried out using HPLC. C18 column (4 mm×250 mm×5 m) was used. The sample was prepared in Methanol and the mobile phase was Methanol and water. A gradient program sequence was used where the run time was 60 minutes and the flowrate were 1 ml/min. The extract obtained is having a minimum of Nimbolide in an amount of 3 mg/gm, Nimbin in an amount of 130 μg/gm and Salinin in an amount of 200 μg/gm.

Example 4

Therapeutically Effective Formulations for Oral Use

Formulation 1

$SCO_2$ *Azadirachta indica* leaf extract: 75 mg (with minimum 0.22 mg Nimbolide; 9.75 μg Nimbin and Salinin 15 μg); naturally occurring antioxidants such as Vitamin E (tocopherols) or Rosemary (*Rosemarinus officinalis*) $CO_2$ extract containing minimum 6% Carnosic acid: 10 mg and Sesame oil: 415 mg; this formulation was filled in a soft gel capsule of 500 mg.

This capsule can be administered to the patient 2-4 times a day (total 150-300 mg of Neem leaf extract per day as an active drug).

Alternatively, a liquid veggy cap is manufactured using 25 mg of $SCO_2$ extract as above with 10 mg of rosemary extract or 10 mg of liquid vitamin E as antioxidant and 465 mg of Sesame oil to administer a daily dose of 150-300 mg per day.

Alternatively, a liquid veggy cap is manufactured using 50 mg of $SCO_2$ extract as above with 10 mg of rosemary extract or 10 mg of liquid vitamin E as antioxidant and 440 mg of Sesame oil to administer a daily dose of 150-300 mg per day.

Formulation 2

$SCO_2$ *Azadirachta indica* leaf extract: 50 mg (with minimum 0.15 mg Nimbolide; 6.5 μg Nimbin and Salinin 10 μg), 582 mg dextrin/malto-dextrin or other naturally occurring carrier (e.g. di-calcium phosphate or any other pharmaceutical grade carrier); and 18 mg aerated or fumed silica.

A free-flowing powder was prepared and encapsulated in suitable size of hard gelatin or vegetarian capsule available in the market. This formulation can be administered 3-4 times a day to get a therapeutic dose of 150-300 mg Neem leaf $CO_2$ extract.

Formulation 3

SCO$_2$ *Azadirachta indica* leaf extract: 50 mg (with minimum 0.15 mg Nimbolide; 6.5 µg Nimbin and Salinin 10 µg), 582 mg of water extract obtained from Neem leaf and 18 mg aerated or fumed silica.

A free-flowing powder was prepared and encapsulated in suitable size of hard gelatin or vegetarian capsule available in the market. This formulation can be administered 3-4 times a day to get a therapeutic dose of 150-300 mg Neem leaf CO$_2$ extract.

Formulation 4

Mouthwash formulation containing SCO$_2$ *Azadirachta indica* leaf extract: 2.28 g (with minimum Nimbolide: 7.2 mg; Nimbin: 296.41 µg and Salinin 456 µg), Peppermint (*Mentha pierita*) oil: 13.81 g, Spearmint (*Mentha spicata*) oil: 9.26 g, Clove Bud (*Syzigium aromaticum*) CO$_2$ oil: 3.98 g, Tween 80: 20.68 g. 1.25 g of the said blend was diluted in 98.75 g in Base. The base contains Water 73.5 g, Aloe Vera water (200×): 10 g, Sorbitol: 10 g, Glycerin: 5.9 g, Ascorbic acid: 0.5 g, Potassium Sorbate: 0.1 g.

A liquid formulation was prepared. The same can be administered 3 times a day, 20 ml each time, to get a therapeutic dose of 15 mg Neem Leaf CO$_2$ extract as described above.

Alternatively, a liposomal water based formulation was prepared using 2 gm of SCO$_2$ extract as above with 95.6 gm of demineralized water with 2 gm of Peppermint oil and 0.2 gm of rosemary CO$_2$ extract to obtain 100 gm of mouthwash formulation with minimum additives with standard pharmaceutical grade emulsifier like "Polysorbate 80" 0.2 gm using a high speed homogenizer.

Example 5

Cancer Preventive Effect of a Super Critical CO$_2$ Neem Extract of Leaf (SCNE):

Cell Viability Assay:

Colorectal cancer cells, HCT116 and HT29 as well as normal Rat Colon cells IEC-6 cells, were plated in 96-well plates, next day the cells were serum starved for 24 hrs and treated with SCNE (0-75 µg/mL) and nimbolide (1-15 µM) for 48 h and 72 h. After treatment, cell viability was measured by MTT [3-(4, 5-Dimethylthiazol-2-yl)-2, 5-Diphenyltetrazolium Bromide] assay (Sigma Aldrich, MO) according to the manufacturer's instructions. Briefly, MTT (5 mg/mL) was added and plates were incubated at 37° C. for 4 h before dimethyl sulfoxide was added to each well. Finally, the absorbance of each well was read at a wavelength of 540 nm using a plate reader (Molecular Devices, Sunnyvale, Calif., USA). The results were expressed as a percentage of surviving cells over non treated cells.

The results confirm that the SCNE is non-toxic to normal Rat Colon cells IEC-6 cells even at higher concentration of 50 µg/mL after 48 hrs (FIG. 1). The SCNE treated colorectal cancer cells, viz., HCT116 and HT29 exhibits 62% (FIG. 2) and 44% cell viability (FIG. 3) respectively at a concentration of 15 µg/mL at the end of 72 hrs and exhibits zero cell viability at a concentration of 40 µg/mL (FIG. 2) and 75 µg/mL (FIG. 3) at the end of 72 hrs. The nimbolide treated colorectal cancer cells, viz., HCT116 (FIG. 4) and HT29 (FIG. 5) exhibits 80% and 75% cell viability respectively at a concentration of 15 µg/mL at the end of 48 hrs.

The above experiment conclusively confirmed that the super critical CO$_2$ neem leaf extract (SCNE extract) comprising a combination of Nimbolide, Nimbin and Salinin possess higher therapeutic efficacy than the Nimbolide alone.

Overall, the data suggests that SCNE effectively suppress the growth of human colorectal cancer through induction of apoptosis via pro-inflammatory pathway and NF-kB inhibition.

We claim:

1. A process for preparation of a CO$_2$ extract of *Azadirachta indica* leaves, comprising:
   a) powdering dried *Azadirachta indica* leaves having a moisture content of less than 12% to obtain a powder comprising particles having a size of less than 0.42 mm;
   b) subjecting the powder of step a) to extraction with supercritical CO$_2$ at a pressure ranging from 80 Bar (80 kg/cm) to 350 Bar (350 kg/cm) at a temperature ranging from 31° C. to 45° C. to obtain a CO$_2$ composition comprising CO$_2$ extractives and a residual powder;
   c) separating the CO$_2$ extractives from the residual powder at a pressure ranging from 40 Bar to 65 Bar at a temperature lower than the extraction temperature to obtain an Extract A;
   d) subjecting the residual powder to further extraction using a mixture of CO$_2$ and ethyl alcohol at a pressure ranging between 80 Bar to 350 Bar and at an extraction temperature ranging from 31° C. to 45° C. to obtain an ethyl alcohol/CO$_2$ composition comprising *Azadirachta indica* extractives;
   e) recovering the *Azadirachta indica* extractives from the ethyl alcohol/CO$_2$ composition as an Extract B by:
      reducing a solvent pressure to between 40 Bar and 65 Bar at a temperature lower than the extraction temperature, followed by
      vacuum distillation of the ethyl alcohol; and
   f) combining the Extract A and the Extract B to obtain the CO$_2$ extract of *Azadirachta indica* leaves.

2. The process as claimed in claim 1, wherein subjecting the powder of step a) to supercritical CO$_2$ extraction is carried out at a flow rate of 10 to 40 kg of CO$_2$ per kg of raw material.

3. The process as claimed in claim 1, wherein the extract A is passed through a high velocity micro-jet or nozzle to obtain particles having a particle size of between 10 nm and 100 nm.

4. The process as claimed in claim 1, wherein the mixture of CO$_2$ and ethyl alcohol contains 3 to 10% of ethyl alcohol, based on the weight of the CO$_2$.

5. The process as claimed in claim 1, wherein the temperature in separating step c) is maintained between 10° C. and 30° C.

6. The process as claimed in claim 1, wherein the temperature in recovering step e) is maintained between 10° C. and 30° C.

7. The process as claimed in claim 1, wherein the vacuum distillation of ethyl alcohol is carried out at a temperature below 45° C.

8. The process as claimed in claim 1, wherein the CO$_2$ extract of *Azadirachta indica* leaves obtained in step f) comprises:
   Nimbolide in a minimum amount of 3 mg/gm;
   Nimbin in a minimum amount of 130 µg/gm; and
   Salinin in a minimum amount of 200 µg/gm.

9. The process as claimed in claim 1, wherein the CO$_2$ extract of *Azadirachta indica* leaves further comprises a minor amount of Desacetylnimbin, Azadiradione, Azdirone, Nimbolin, Nimbinene, or a mixture thereof.

* * * * *